United States Patent [19]

Sakata et al.

[11] Patent Number: 5,183,882
[45] Date of Patent: Feb. 2, 1993

[54] 2'-DEOXY-2'-METHYLIDENECYTIDINE DIHYDRATE, METHODS FOR ITS PRODUCTION AND COMPOSITIONS

[75] Inventors: Shinji Sakata; Takanori Miyashita, both of Choshi; Kazuhiko Kondo, Sapporo; Atsushi Sakai; Toshiyuki Shibata, both of Nakatsu; Takayuki Ogawa, Chikujo, all of Japan

[73] Assignees: Yoshitomi Pharmaceutical Industries, Ltd., Osaka; Yamasa Shoyu Co., Ltd., Chiba, both of Japan

[21] Appl. No.: 656,824

[22] Filed: Feb. 19, 1991

[30] Foreign Application Priority Data

Feb. 19, 1990 [JP] Japan ................... 2-37695

[51] Int. Cl.⁵ ............... C04H 19/06; A61K 31/70; A61K 47/26
[52] U.S. Cl. ..................... 514/49; 536/28.5
[58] Field of Search ................. 536/4.1, 23

[56] References Cited

U.S. PATENT DOCUMENTS 5,026,835  6/1991  Ueda et al. ............. 536/23
5,047,520  9/1991  Matsuda et al. ......... 536/23

FOREIGN PATENT DOCUMENTS 0310673  3/1988  European Pat. Off.

OTHER PUBLICATIONS

Chemical Abstracts, vol. 110, No. 18, May 1, 1989, p. 405, abstract No. 160409h, Columbus, Ohio, US; & JP-A-63 258 818 (Yoshitomi Pharmaceutical Industries, Ltd) 26-10-1988.
"Journal of Medicinal Chemistry", 31 [1063-1064 (1988)] Takenuki et al.

Primary Examiner—Nathan M. Nutter
Attorney, Agent, or Firm—Wenderoth, Lind & Ponack

[57] ABSTRACT

Novel stable, non-hygroscopic 2'-deoxy-2'-methylidenecytidine dihydrate and its methods for production, and compositions with improved solubility containing same and saccharide(s).

8 Claims, No Drawings

2'-DEOXY-2'-METHYLIDENECYTIDINE DIHYDRATE, METHODS FOR ITS PRODUCTION AND COMPOSITIONS

BACKGROUND OF THE INVENTION

The present invention relates to novel 2'-deoxy-2'-methylidenecytidine dihydrate (hereinafter referred to as DMDC $2H_2O$), methods for its production and compositions containing the DMDC $2H_2O$ which are stable and improved in solubility.

BACKGROUND ART

DMDC shown by the following formula has excellent antitumor and antiviral activities. DMDC has been heretofore prepared into acid addition salts such as hydrochloride, etc. [See EP-A 310 673 and J. Med. Chem., 31, 1063-1064 (1988)]

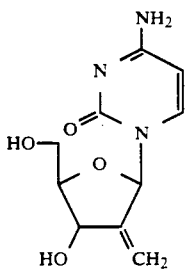

However, DMDC hydrochloride which is obtained as crystals is hygroscopic and unstable. For example, when DMDC hydrochloride is stored at 30° C. in a relative humidity of 92%, it is gradually decomposed, giving rise to a stability problem. Such lack of stability is prominent when DMDC hydrochloride is dissolved in water, as shown by the residual percent of DMDC after keeping DMDC hydrochloride dissolved in water, at room temperature (25° C.) for 10 days, which is about 70%.

The drawback of DMDC hydrochloride in hygroscopicity and poor stability constitutes a major obstacle in formulating pharmaceutical compositions containing DMDC hydrochloride as an active ingredient. It leads to necessity of special production apparatuses provided with a means for prevention of humidity and tight packaging of the pharmaceutical compositions thus produced. Further, the poor stability inevitably results in a composition which deteriorates in a short time, and specifically, the formulation of liquid compositions is substantially unattainable.

Under these problems, the pharmaceutical compositions of DMDC hydrochloride have been, despite their usefulness in respect to pharmacological activities, unobtainable without a special means for formulating these compositions.

SUMMARY OF THE INVENTION

In an attempt to overcome the aforementioned problems, the present inventors have made intensive studies and found that novel DMDC $2H_2O$ is non-hygroscopic and is extremely stable.

In addition, the inventors have found that while the solubility of DMDC $2H_2O$ in water or various buffers is relatively low (1.2-1.7%), compositions of DMDC $2H_2O$ with high stability can be obtained by adding saccharide(s) thereto and that the compositions are highly soluble in an aqueous solution, specifically an aqueous solution containing organic acid(s), and the DMDC remains stable in the solution.

That is, the invention provides:
(1) DMDC $2H_2O$, especially crystalline DMDC $2H_2O$.
(2) Methods for producing DMDC $2H_2O$ which comprise removal of substance(s) (including ions) except DMDC, hydrogen ions and hydroxy ions from an aqueous solution containing DMDC, followed by crystallization from water.
(3) Methods for producing DMDC $2H_2O$ which comprise removal of substance(s) (including ions) except DMDC, hydrogen ions and hydroxy ions from an aqueous solution containing DMDC, and concentrating the resulting solution to give a solid, followed by crystallization thereof from water.
(4) Compositions containing DMDC $2H_2O$ and saccharide(s), preferably those obtained by lyophilization of an aqueous solution containing DMDC $2H_2O$ and saccharide(s) or copulverization of DMDC $2H_2O$ and saccharide(s) both in solid state.

DETAILED DESCRIPTION OF THE INVENTION

The physiochemical properties of the DMDC $2H_2O$ and methods for producing it are described in detail in the following.

I. Physiochemical properties (1) powder X-ray diffraction pattern

The DMDC $2H_2O$ obtained as crystals shows the following X-ray diffraction patterns under the conditions of target: Cu, voltage: 50 KV and current: 30 mA.

| Spacing d (Å) | Relative Intensities |
| --- | --- |
| 2.90 | 40 |
| 3.08 | 47 |
| 3.29 | 54 |
| 3.71 | 100 |
| 3.89 | 35 |
| 4.08 | 91 |
| 5.73 | 31 |
| 7.51 | 66 |
| 7.79 | 56 |

(2) Hygroscopicity

The DMDC $2H_2O$ did not show a weight change after keeping same at 30° C. in a relative humidity of 92% for 6 days in open exposure, showing substantially no hygroscopicity. After leaving the DMDC $2H_2O$ as above, the water content was measured by loss in a drying method and Karl Fischer's method. The water content of the DMDC $2H_2O$ was 13.1% and 13.4% by each method, which coincide with the theoretical value (13.09%) of DMDC $2H_2O$. The measurement of the water content by loss in the drying method and the Karl Fischer's method was conducted according to the method described in Japan Pharmacopoeia, 11th Edition, p. B-60 and p. B-179, issued by the Society of Japanese Pharmacopoeia.

(3) Stability

The DMDC $2H_2O$ dissolved in distilled water (0.04%, pH 7.0) was used as a test solution and the solution was kept standing at 25° C. for 240 hours or at 60° C. for 1 hour to examine the stability of the DMDC $2H_2O$ in an aqueous solution. DMDC hydrochloride dissolved in distilled water (0.1%, pH 3.2) was used as control, which was kept standing at 25° C. for 672 hours. The results show no decomposition of the DMDC 2H₂O, confirming high stability of the DMDC 2H₂O (See Table 1).

TABLE 1

| | Temperature (°C.) | Time (hours) | Residual rate (%) |
|---|---|---|---|
| DMDC 2H₂O | 25 | 0 | 100.0 |
| | | 1 | 100.0 |
| | | 24 | 100.0 |
| | | 48 | 99.9 |
| | | 96 | 99.9 |
| | | 144 | 99.9 |
| | | 240 | 99.8 |
| | 60 | 1 | 100.0 |
| Control | 25 | 0 | 98.0 |
| | | 24 | 97.5 |
| | | 48 | 93.3 |
| | | 168 | 82.3 |
| | | 312 | 71.5 |
| | | 672 | 41.0 |

Analytical Conditions
Column: Innertosyl ODS-2 (Gaschro Kogyo)
Eluent: 50 mM tetraethylammonium acetate buffer (pH 7.0, containing 0.2% acetonitrile)
Detection: 270 nm
Flow rate: 1 ml/minute
(4) Melting point
The melting point of the DMDC 2H₂O of the invention is about 107°-110° C.
(5) Elemental analysis Calculated (%) C: 43.63, H: 6.23, N: 15.27; Found (%) C: 43.53, H: 6.22, N: 15.26.
II. Methods for producing DMDC 2H₂O
The DMDC used for producing the DMDC 2H₂O of the invention can be prepared by the methods disclosed in EP-A 310 673, for example, from cytidine by a series of reaction processes comprising ① introduction of protective groups, ② oxidation of the 2'-hydroxy group, ③ methylidenation of the 2'-keto group and ④ removal of the protective groups. Such reaction processes are shown in the schematic flow in the following.

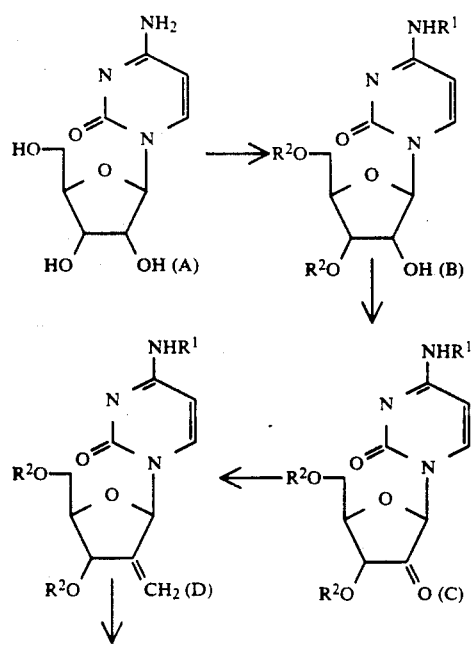

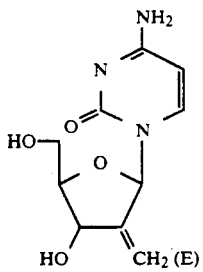

wherein R¹ and R² are protective groups.

The reaction mixture after removal of the protective groups may be directly used for preparing the DMDC 2H₂O as an aqueous solution containing DMDC, or an acid addition salt of DMDC may be obtained from said reaction mixture by a conventional means (e.g. various chromatographys, recrystallization, etc.).

The DMDC 2H₂O is prepared by removing substance(s) (including ions) as completely as possible except DMDC, hydrogen ions and hydroxy ions from an aqueous solution containing DMDC, followed by crystallization from water, preferably distilled water. Particularly, purer crystals can be obtained if a method wherein substance(s) (including ions) except DMDC, hydrogen ions and hydroxy ions is(are) removed as completely as possible from an aqueous solution containing DMDC, and the solution thus obtained is concentrated to give a solid which is then crystallized from water, is adopted.

There is no limitation involved in an aqueous solution containing DMDC as long as the solution contains DMDC, and usable is anhydride of DMDC or an acid addition salt of DMDC (e.g. hydrochloride, sulfate, hydrobromide, phosphate, maleate, fumarate, tartrate, succinate, citrate, p-toluenesulfonate, etc.) dissolved in water. Further, a reaction mixture per se produced in the course of preparing DMDC by deprotection and/or amination of the final synthesis intermediates in DMDC synthesis by a conventional method (e.g. 2'-deoxy-2'-methylidene-N⁴-acylcytidine, 2'-deoxy-2'-methylidene-4-O-alkyluridine, etc.) may be used as an aqueous solution containing DMDC.

The method for removing substance(s) and ions except DMDC, hydrogen ions and hydroxy ions from an aqueous solution containing DMDC is not particularly limited and a suitable method may be selected depending on the substance(s) to be removed. For example, chloride ions (Cl⁻) in the solution can be removed by bringing DMDC hydrochloride in water, which is be used as an aqueous solution containing DMDC, into contact with an anion-exchange resin [e.g. Amberlite 402 (OH type), etc.].

When the reaction mixture wherein DMDC has been prepared by reacting concentrated ammonia water with 2'-deoxy-2'-methylidene-N⁴-benzoylcytidine is used as an aqueous solution containing DMDC, benzoic acid in the solution can be removed by bringing the solution into contact with an anion-exchange resin.

Concentration of the solution from which substance(s) (including ions) except DMDC, hydrogen ions and hydroxy ions has(have) been removed affords a solid such as crude crystals.

In case where the substance(s) to be removed is(are) have volatile properties, an aqueous solution containing DMDC is subjected to a dehydration treatment, preferably lyophilization, to simultaneously conduct removal of the substance(s) except DMDC, hydrogen ions and hydroxy ions and subsequent concentration.

The solid thus obtained is dissolved in water, preferably distilled water, while heating at 80°-100° C., and cooled to about 30° C. by stirring to give DMDC 2H$_2$O as crystals.

The DMDC 2H$_2$O of the invention is washed with a small amount of water, and dried by a conventicnal method used for drying a normal crystalline compound (e.g. clean air bath, etc.), if desired.

The DMDC 2H$_2$O shows the same pharmacological activities as of known DMDC hydrochloride, while possessing far superior physical properties showing substantially no hygroscopicity and high stability in both solid state and liquid state as compared to DMDC hydrochloride, and is extremely useful as an active ingredient for antitumor or antiviral agents. In addition, the compositions containing the DMDC 2H$_2$O and saccharide(s) are stable, and exhibit high solubility in an aqueous solution of organic acid(s).

As the saccharide(s) used for improving solubility of the DMDC 2H$_2$O in an aqueous solution, there may be mentioned monosaccharides or disaccharides such as glucose, D-sorbitol, D-mannitol, lactose, fructose, sucrose, etc., which is(are) preferably used in an amount of 0.5 to 3-fold by weight relative to the DMDC 2H$_2$O.

The compositions of the invention can be prepared by lyophilizing an aqueous solution containing DMDC 2H$_2$O and saccharide(s) or co-pulverizing DMDC 2H$_2$O and saccharide(s) in a solid state. When lyophilized compositions are desired, an aqueous solution containing DMDC 2H$_2$O and saccharide(s) is sterilized by filtration, filled in a vial and subjected to vacuum lyophilization. After nitrogen displacement, the vial is rubber plug-sealed and provided with an aluminium seal. When co-pulverized compositions are desired, DMDC 2H$_2$O and saccharide(s) are co-pulverized with a mortar or a hammermill. The conditions and the degree of pulverization are known and are not particularly limited.

The lyophilized compositions or co-pulverized compositions thus obtained can be stored as they are at room temperature for a long period, and when in use, an aqueous solution of organic acid(s) (preferably at least one species) selected from lactic acid, citric acid, maleic acid, tartaric acid, acetic acid, etc. (0.1-20 w/v %, preferably 0.5-10 w/v %) is preferably used as a dissolution medium. The aqueous solution of organic acid(s) is used in an amount of 10- to 50-fold amount relative to the DMDC 2H$_2$O. A pharmaceutically acceptable solvent (e.g. propylene glycol, polyethylene glycol 400, etc.), dissolution adjuvant (ethanol, polyoxyethylene, hydrogenated castor oil 60, etc.), buffer (sodium lactate, sodium citrate, etc.), preservative (methyl p-hydroxybenzoate, propyl p-hydroxybenzoate, etc.), pH adjuster (hydrochloric acid, sodium hydroxide, etc.), or the like may be added to the dissolution medium, if necessary.

The invention affords antitumor compositions which are stable after a long term storage. The compositions are rapidly dissolved, enabling formulation of liquid preparations containing DMDC 2H$_2$O at a concentration of not less than 20 mg/ml, preferably not less than 50 mg/ml. The liquid compositions thus obtained can be kept stably at room temperature.

The invention is described in detail by way of working examples in the following.

EXAMPLE 1

DMDC hydrochloride (1 g) mentioned in EP-A 310 673 was dissolved in distilled water (100 ml) and the mixture was brought into contact with an anion-exchange resin Amberlite 402 (OH type) (Rhome and Haas Co.).

After the contact, the anion exchange resin was filtered off and the filtrate was concentrated under reduced pressure to give crude crystal(s).

The crude crystals were added to distilled water heated to 80° C. while stirring for dissolution. The mixture was gradually cooled to 30° C. while stirring to precipitate crystals to give DMDC 2H$_2$O.

The physiochemical properties of the obtained DMDC 2H$_2$O were the same as mentioned above.

EXAMPLE 2

To 2'-deoxy-2'-methylidene-N$^4$-benzoylcytidine (3.4 g, 10 mmol) as in the above EP-A in dimethylformamide (30 ml) was added con. ammonia water (30 ml), and the mixture was sealed and stirred for 24 hours. The reaction mixture was diluted with water (400 ml), passed through an Amberlite IRA-402 column (OH type, 100 ml), followed by elution with water. Thereafter, the eluted fractions of DMDC were collected and concentrated. The crude crystals (2.1 g) thus obtained were washed with acetone and recrystallized from distilled water (35 ml) to give 1.7 g of DMDC 2H$_2$O as crystal(s) (yield 61%).

EXAMPLE 3

To sterile distilled water for injection (2 l) were added DMDC 2H$_2$O (40 g) and D-mannitol (40 g) for dissolution. The solution was sterilized by filtration, and 12.5 ml therefrom was filled in a 20 ml-volume vial. The vial was freezed at −35° C. and subjected to vacuum lyophilization at −20° C. The blank of the vial was filled with nitrogen gas, sealed with a rubber plug and provided with an aluminium seal to give a rapidly soluble lyophilized pharmaceutical composition of DMDC 2H$_2$O.

EXAMPLE 4

To sterile distilled water for injection (2 l) were added DMDC 2H$_2$O (40 g) and glucose (40 g) for dissolution. The solution was sterilized by filtration, and 12.5 ml therefrom was filled in a 20 ml-volume vial. The vial was freezed at −35° C. and subjected to vacuum lyophilization at −20° C. The blank of the vial was filled with nitrogen gas, sealed with a rubber plug and provided with an aluminium seal to give a rapidly soluble lyophilized pharmaceutical composition of DMDC 2H$_2$O.

EXAMPLE 5

After DMDC 2H$_2$O (20 g) prepared under sterile conditions and D-sorbitol (20 g) were co-pulverized with a hammermill, 500 mg of which was weighed out, packed in an ampoule and sealed to give a product.

EXAMPLE 6

After DMDC 2H$_2$O (20 g) prepared under sterile conditions and lactose (20 g) were co-pulverized with a hammermill, 500 mg of which was weighed out, packed in an ampoule and sealed to give a product.

EXAMPLE 7

After DMDC 2H$_2$O (20 g) prepared under sterile conditions and fructose (20 g) were co-pulverized with a hammermill, 500 mg of which was weighed out, packed in an ampoule and sealed to give a product.

EXAMPLE 8

After DMDC 2H$_2$O (20 g) prepared under sterile conditions and sucrose (20 g) were co-pulverized with a hammermill, 500 mg of which was weighed out, packed in an ampoule and sealed to give a product.

EXAMPLE 9

To each pharmaceutical composition (500 mg) of DMDC 2H$_2$O packed in vials or ampoules in Examples 3 to 8 was added 10 ml of 1 w/v % aqueous lactic acid for dissolution to give injections of DMDC 2H$_2$O. The same procedure was repeated using 3 w/v % aqueous citric acid, 5 w/v % aqueous maleic acid, 6 w/v % aqueous tartaric acid or 10 w/v % aqueous acetic acid to give injections of DMDC 2H$_2$O.

EXPERIMENT EXAMPLE 1

DMDC 2H$_2$O (1 part by weight) and glucose, D-sorbitol or D-mannitol (0.5 to 3 parts by weight) were co-pulverized with a mortar, to which (an equivalent amount to 125 mg of DMDC 2H$_2$O) was added 5 ml of 1 w/v % aqueous lactic acid. The mixture was shaken, and the time necessary for dissolution was measured. In the case where saccharide(s) is (are) not contained, it took 2 minutes to dissolve. On the other hand, the dissolution time of the composition prepared by co-pulverization with glucose, D-sorbitol or D-mannitol was shortened to 0.75 minute. No effect of the weight ratio of the saccharide(s) on DMDC 2H$_2$O was observed.

EXPERIMENT EXAMPLE 2

DMDC 2H$_2$O (1 part by weight) and D-mannitol (0.5 to 2 parts by weight) were lyophilized or co-pulverized with a hammermill, to which (an equivalent amount to 125 mg of DMDC 2H$_2$O) was added 5 ml of 1 w/v % aqueous lactic acid. The mixture was shaken, and the time necessary for dissolution was measured. A physical mixture of the same ingredients mixed by passing through a No. 30 sieve and a sample without D-mannitol, and without lyophilization and co-pulverization were tested in the same manner. The results are summarized in Table 2.

TABLE 2

Results of dissolution time measurement
(Effects of amount of D-mannitol added and treatment method)

| Weight ratio of D-mannitol to DMDC 2 H$_2$O (being 1) | Treatment method | Dissolution time |
|---|---|---|
| 0.5 | pulverization with a hammermill | 0.6 min. |
|  | lyophilization | 0.6 min. |
| 1 | pulverization with a hammermill | 0.6 min. |
|  | lyophilization | 0.5 min. |
| 2 | pulverization with a hammermill | 0.6 min. |
|  | lyophilization | 0.5 min. |
| 1 | physical mixture | 2 mins. |
| non-added | no treatment | 5 mins. |

As is evident from the results in Experiment Examples 1 and 2, the dissolution rate was remarkably enhanced by lyophilization or co-pulverization with saccharide(s) as compared with that of the physical mixture or the non-added, non-treated sample. Particularly, the dissolution time was shortened to 0.5 minute by lyophilization with D-mannitol in an amount not less than equivalent by weight to DMDC 2H$_2$O.

EXPERIMENT EXAMPLE 3

To a preparation obtained by adding D-mannitol (250 mg) to DMDC 2H$_2$O (250 mg) and lyophilizing was added 5 ml of 1 w/v % aqueous lactic acid or 5 ml of 1 w/v % aqueous citric acid. The mixtures were shaken, and the dissolution time was measured. Both of them dissolved in 0.5 minute.

EXPERIMENT EXAMPLE 4

A co-pulverized composition of DMDC 2H$_2$O and D-mannitol in the ratio of 1:2 by weight was stored at room temperature, 40° C. or 60° C. Their appearance was observed, decomposition of DMDC 2H$_2$O was checked with TLC and the content of DMDC 2H$_2$O was measured by HPLC method (detected at 270 nm) at given time intervals. The results are summarized in Table 3.

TABLE 3

Stability of the co-pulverized composition of DMDC 2H$_2$O and D-mannitol

| experiment conditions (container) | storage time | appearance | TLC | content (%) |
|---|---|---|---|---|
| initial state |  | white crystalline powder | normal | 99.7 |
| room temperature (tight container) | 1 mo. | no change | no change | 100.3 |
|  | 2 mos. | no change | no change | 100.9 |
|  | 3 mos. | no change | no change | 100.7 |
| 40° C. (tight container) | 1 wk | no change | no change | 100.5 |
|  | 2 wks | no change | no change | 99.1 |
| 60° C. (tight container) | 2 wks | no change | no change | 101.1 |
|  | 4 wks | no change | no change | 101.3 |

As is evident from the above results, it is speculated that the co-pulverized composition of DMDC 2H$_2$O and D-mannitol is stable for a long time by storage at room temperature.

EXPERIMENT EXAMPLE 5

To a co-pulverized composition of DMDC 2H$_2$O (250 mg) and D-mannitol (500 mg) was added 10 ml of 1 w/v % aqueous lactic acid or 10 ml of 1 w/v % aqueous citric acid. After dissolution, the solutions were stored at room temperature. Their appearance was observed, the decomposition of DMDC 2H$_2$O was checked with TLC and the content of DMDC 2H$_2$O was measured by HPLC method (detected at 270 nm) at given time intervals. The results are summarized in Table 4.

TABLE 4

Stability of DMDC 2H$_2$O in lactic acid medium or citric acid medium at a concentration of 2.5%

| dissolving medium | storage conditions | storage time | appearance | TLC | content (%) |
|---|---|---|---|---|---|
| lactic acid | initial state |  | colorless, clear | normal | 102.4 |
|  | room temp. | 4 hs | no change | no change | 102.3 |
| citric acid | initial state |  | colorless, clear | normal | 100.6 |
|  | room temp. | 4 hs | no change | no change | 100.8 |

As is evident from the above results, the solutions remained stable for 4 hours after dissolution at room temperature.

What is claimed is:

1. A composition which is obtained by liophylization of an aqueous solution containing 2'-deoxy-2'-methylidenecytidine dihydrate and saccharide(s).

2. A composition which is obtained by co-pulverization of 2'-deoxy-2'-methylidenecytidine dihydrate and saccharide(s).

3. A composition as claimed in claim 1 or 2, wherein the saccharide(s) is (are) monosaccharides or disaccharides.

4. A composition as claimed in claim 3, wherein the saccharide(s) is (are) selected from the group consisting of glucose, D-sorbitol, D-mannitol, lactose, fructose and sucrose.

5. A composition as claimed in claim 1 or 2 wherein an aqueous solution of organic acid(s) is used as a dissolution medium in formulation of a liquid preparation.

6. A composition as claimed in claim 5, wherein the aqueous solution of organic acid(s) contains one or more species selected from the group consisting of lactic acid, citric acid, maleic acid, tartaric acid and acetic acid.

7. A method for producing 2'-deoxy-2'-methylidenecytidine dihydrate, which comprises contacting an aqueous solution containing 2'-deoxy-2'-methylidenecytidine with an anion-exchange resin and concentrating the resulting solution to produce a solid, followed by crystallization of the solid from water.

8. A method for producing crystalline 2'-deoxy-2'-methyli- denecytidine dihydrate, which comprises contacting an aqueous solution containing 2'-deoxy-2'-methylidenecytidine with an anion-exchange resin, and concentrating the resulting solution to produce a solid, followed by crystallization of the solid from water.

* * * * *